US 7,835,491 B2

(12) United States Patent
Fischer et al.

(10) Patent No.: US 7,835,491 B2
(45) Date of Patent: Nov. 16, 2010

(54) TOMOSYNTHETIC IMAGE RECONSTRUCTION METHOD AND APPARATUS

(75) Inventors: Daniel Fischer, Erlangen (DE); Jasmina Ludwig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 100 days.

(21) Appl. No.: 12/369,238

(22) Filed: Feb. 11, 2009

(65) Prior Publication Data
US 2009/0207969 A1 Aug. 20, 2009

(30) Foreign Application Priority Data
Feb. 14, 2008 (DE) .................. 10 2008 009 128

(51) Int. Cl.
*A61B 6/04* (2006.01)
(52) U.S. Cl. ............................. 378/37; 378/4
(58) Field of Classification Search ............ 378/4, 378/37
See application file for complete search history.

(56) References Cited

U.S. PATENT DOCUMENTS

| | | | | |
|---|---|---|---|---|
| 5,872,828 A | * | 2/1999 | Niklason et al. | 378/23 |
| 6,014,452 A | * | 1/2000 | Zhang et al. | 382/132 |
| 6,075,879 A | * | 6/2000 | Roehrig et al. | 382/132 |
| 7,148,903 B2 | | 12/2006 | Brunner et al. | |
| 2003/0095695 A1 | * | 5/2003 | Arnold | 382/131 |
| 2003/0194049 A1 | | 10/2003 | Claus et al. | |
| 2004/0052328 A1 | * | 3/2004 | Sabol et al. | 378/37 |
| 2007/0003124 A1 | * | 1/2007 | Wood et al. | 382/131 |
| 2008/0247624 A1 | | 10/2008 | Scholz | |

* cited by examiner

*Primary Examiner*—Edward J Glick
*Assistant Examiner*—Alexander H Taningco
(74) *Attorney, Agent, or Firm*—Schiff Hardin LLP

(57) ABSTRACT

To generate a tomosynthetic 3D x-ray image composed of a number of slice images, a tomosynthetic 3D intermediate image composed of a number of slice images is reconstructed from 2D projection images that have not been noise-filtered. The microcalcium regions contained in these slice images are segmented, and one or more subject slice images relevant to these microcalcium voxels are determined for each microcalcium region. The microcalcium voxels belonging to the segmented microcalcium region in this subject slice image or in these subject slice images are projected forwards in the 2D projection images, and the microcalcium pixels associated with these microcalcium voxels are marked in the 2D projection images. Noise-filtered 2D projection images are subsequently generated by subjecting the microcalcium pixels of the 2D projection images to no noise filtering or a noise filtering that leads to a noise reduction reduced relative to the remaining image regions. The tomosynthetic 3D x-ray image is then calculated from the 2D projection images that have been noise-filtered in this manner.

7 Claims, 3 Drawing Sheets

TOMOSYNTHETIC IMAGE RECONSTRUCTION METHOD AND APPARATUS

BACKGROUND OF THE INVENTION

1. Field of the Invention

The present invention concerns a tomosynthetic image reconstruction method, in particular such a method suitable for mammography, in which a tomosynthetic 3D x-ray image is assembled from a number of digital 2D projection images acquired from various projection angles. Moreover, the invention concerns a diagnostic apparatus operating with such a method.

2. Description of the Prior Art

Mammography is an x-ray examination of the female breast, with the goal of detecting tumors in as early a stage as possible. Through steady improvement in mammography methods it is intended to generate x-ray images with good clarity in order to differentiate benign from malignant variations, and to reduce the number of incorrect findings (i.e. the number of suspicious findings that are caused by non-malignant variations) and the number of undetected malignant tumors. In conventional x-ray mammography, a two-dimensional single image of the compressed breast is generated in a single projection direction. Since the tissue layers lying atop one another in the direction of the x-ray beam are superimposed in such a projection, strongly absorbent benign structures can overlap a malignant tumor and complicate the ability to detect such a tumor.

In order to avoid this problem, mammography methods (known as tomosynthesis) are known in which 2D projection images or 2D projection data of the female breast are acquired in a number of different projection directions with a digital x-ray detector. Using image reconstruction methods, a three-dimensional image data set composed of a number of slices images, which respectively reproduce a slice of the breast oriented parallel to the acquisition surface of the x-ray detector, can be generated from 2D projection images (i.e. from the image data belonging to these 2D projection images) acquired from different projection angles. Such an image data set acquired by such reconstruction is designated in the following as a tomosynthetic 3D x-ray image. Tissue structures that lie deeper (as viewed in the propagation direction of the x-ray beam) can be better detected with this technique.

In the generation of the individual 2D projection images, the total dose allowed for a mammography exposure cannot be exceeded, such that these individual 2D projection images must be acquired with a dose that amounts to only a fraction of the permissible total dose (depending on the number of the 2D projection images used for the reconstruction), such that the individual 2D projection images are very noisy. In order to avoid transferring this high image noise to the tomosynthetic 3D x-ray image in the reconstruction, it is possible in principle to subject the individual 2D projection images to a noise-reducing image processing method before the reconstruction. Such a noise-reduction of the 2D projection images, however, has the result that the micro-calcifications necessary for a correct finding and indicative of an early tumor stage either disappear or, in the event that these exist in a cluster, merge with one another and appear as a larger benign calcium deposit in the reconstructed slice. This can lead to a misdiagnosis.

SUMMARY OF THE INVENTION

An object of the present invention is to provide a tomosynthetic image reconstruction method with which it is possible to generate low-noise tomosynthetic 3D x-ray images in which micro-calcifications can still be properly identified. A further object of the invention is to provide a diagnostic apparatus operating with such a method.

The first cited object is achieved according to the invention by a tomosynthetic image reconstruction method wherein, as explained above, a tomosynthetic 3D x-ray image comprised of a number of slice images is generated from a number of digital 2D projection images acquired from different projection angles in a limited angle range. In accordance with the invention the following steps are implemented:

a) reconstruction of a tomosynthetic 3D intermediate image composed of a number of slice images from the 2D projection images that have not been noise-filtered, b) segmentation of microcalcium regions contained in the slice images and marking of the microcalcium voxels respectively associated with these microcalcium region, c) selection or one or more slice images for each of these microcalcium regions as a subject slice image or as subject slice images relevant to this microcalcium region, d) forward projection of the microcalcium voxels belonging to the segmented microcalcium region in the subject slice image or images in the 2D projection images, and marking of the microcalcium pixels associated with these microcalcium voxels in the 2D projection images, e) generation of noise-filtered 2D projection images by subjecting the microcalcium pixels of the 2D projection images either to no noise filtering or a noise filtering that leads to a noise reduction reduced relative to the remaining image regions, f) generation of tomosynthetic 3D x-ray image from the noise-filtered 2D projection images.

The reconstruction of a reduced-noise tomosynthetic 3D x-ray image is possible by these measures, in which 3D x-ray image possibly extant, diagnostically relevant microstructures (microcalcifications) that primarily increasingly occur in one or more slices (the subject slice or the subject slices) can be identified as before.

If the marked image regions are edge-filtered, the ability to detect the microcalcifications in the individual slices is improved.

In a further advantageous embodiment of the invention, the tomosynthetic 3D intermediate image and the tomosynthetic 3D x-ray image are reconstructed using filtered back-projection.

The second cited object is achieved in accordance with the present invention by a diagnostic apparatus having an evaluation device that processes detector signals provided by the x-ray apparatus, the evaluation device being configured, such as by software, to reconstruct a tomosynthetic 3D x-ray image in accordance with the method described above, including all embodiments described above.

DESCRIPTION OF THE PREFERRED EMBODIMENTS

Figure 1:
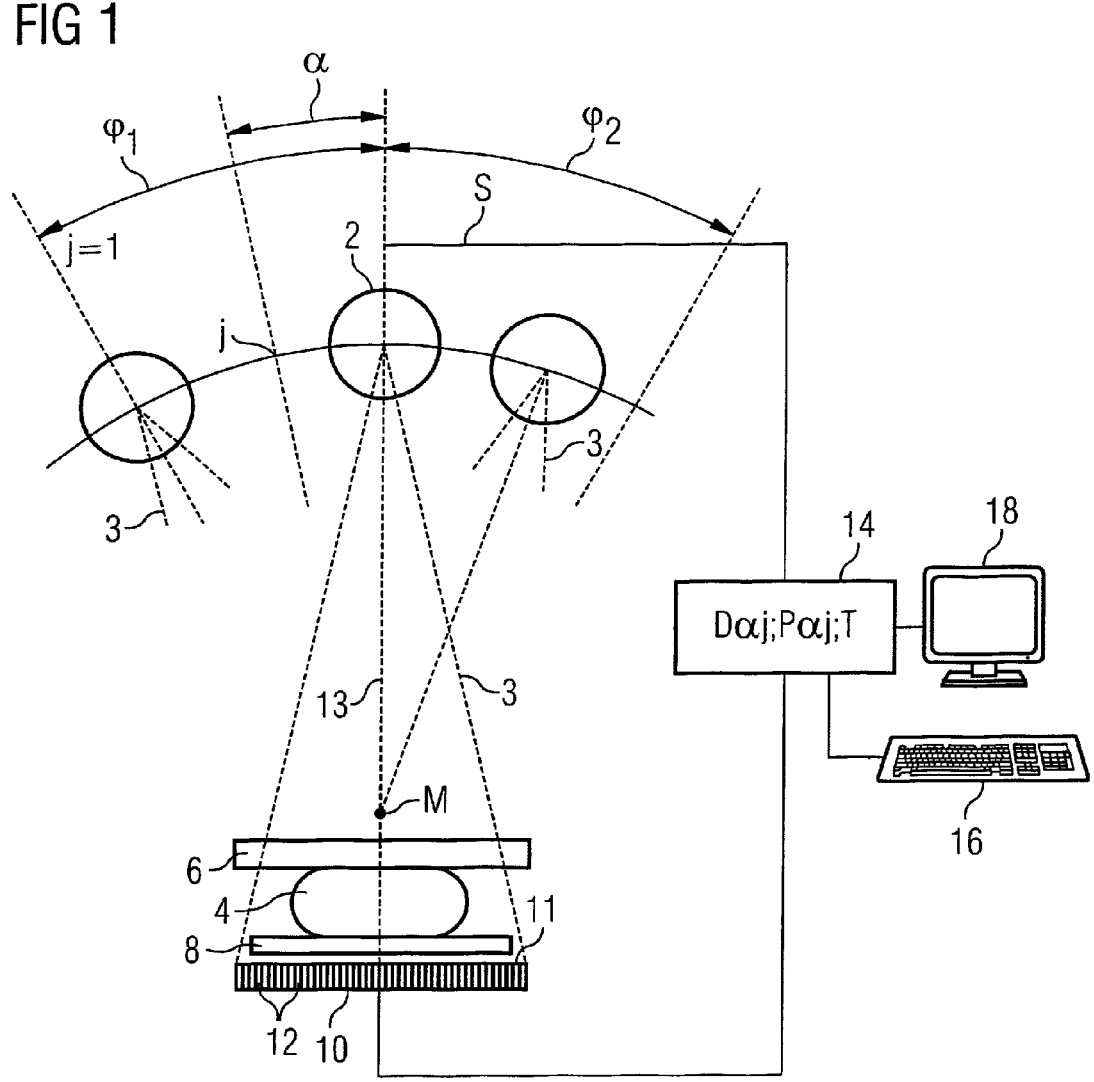
FIG. 1 schematically illustrates an embodiment of an apparatus constructed and operating in accordance with the present invention.

According to FIG. 1, the device (a mammography apparatus in the exemplary embodiment) comprises an x-ray tube 2 to generate x-ray beams 3 that pass through an examination subject 4. The examination subject 4 is a female breast that is held between a compression plate 6 and a support plate 8. The x-rays 3 passing through the examination subject 4, the compression plate 6 and the support plate 8 are received by a large-surface digital x-ray detector 10 that is composed of a number of individual detectors 12 arranged in a matrix array. The acquisition surface 11 of the x-ray detector 10 is parallel to the compression plates 6, 8.

The x-ray tube 2 is mounted such that it can varied in terms of location in a limited region relative to the examination subject and, for example, can be pivoted into different angle positions j=1 . . . n in a limited angle range $\phi1, \phi2$ around an axis M perpendicular to the plane of the drawing, such that 2D projection data sets $D_{\alpha j}$ for different projection angles $\alpha j$ can be generated from the examination subject 4 with varying projection angles $\alpha j$ relative to the normal 13 of the acquisition surface 11 of the x-ray detector 10. 2D projection images $P_{\alpha j}$ are generated from these 2D projection data sets $D_{\alpha j}$ via pre-preparation (for example scaling, i.e. mapping to the greyscale values that can be shown on a monitor 18) in a control and evaluation device 14 containing an image computer. The angle range $\phi1, \phi2$ does not need to be symmetrical relative to the normal 13. These 2D projection images $P_{\alpha j}$ are assembled by reconstruction in the image computer into a tomosynthetic 3D x-ray image T that is presented on the monitor 18. The x-ray detector 10 in this embodiment is stationary during the pivot movement of the x-ray tube 2, but it is also possible to mutually pivot or to linearly displace the x-ray detector, tracking the pivot movement of the x-ray tube 2.

Movement of the x-ray tube 2 on a limited, linear track instead of the pivot is also permissible, such that the height difference between x-ray detector 10 and x-ray tube remains constant. This linear track need not necessarily run symmetrically relative to the normal 13. Given such linear movement, alignment of the x-ray tube 2 on the examination subject 4 ensues so that in this case individual images of the examination subject 4 are also acquired from different projection angles $\alpha_j$ but in a limited angle range.

The control of the angle position j (or, in the case of a linear displacement and the alignment of the x-ray tube 2, its operating parameters as well) ensues based on control signals A that are generated by the control and evaluation device 14. Various image reconstruction variants explained in the following can be selected and implemented by the user through input elements (symbolically illustrated in the example by a keyboard 16).

Figure 2:
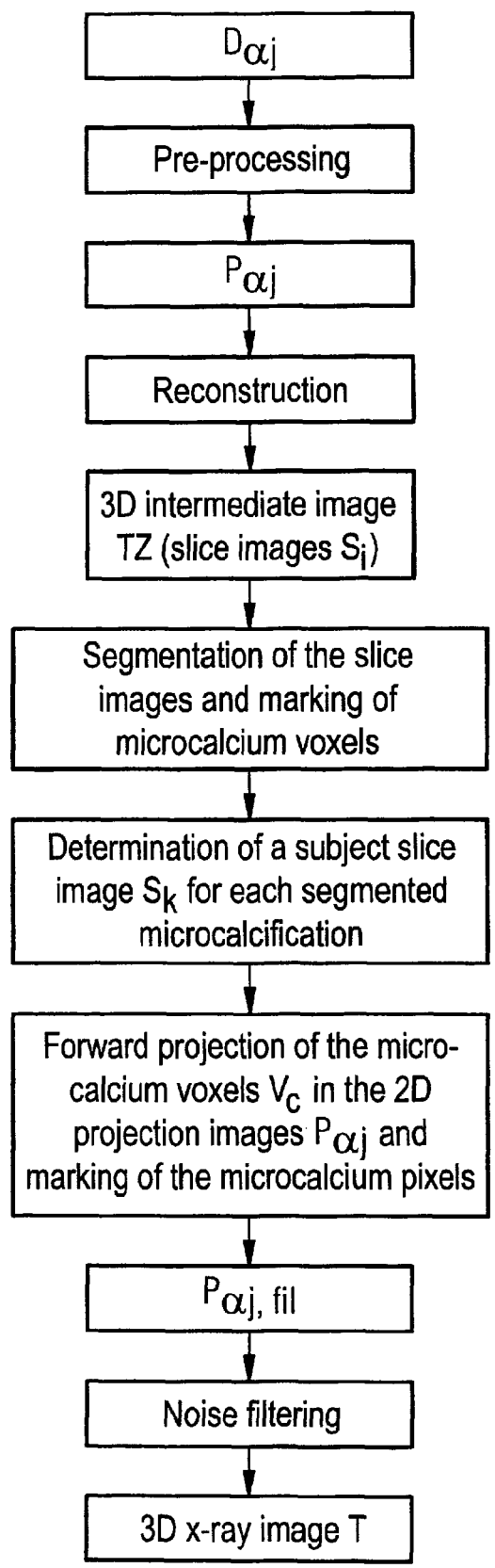
FIG. 2 is a flowchart illustrating an embodiment of the method according to the invention.

According to FIG. 2, the tomosynthetic 3D intermediate image TZ constructed from a number of slice images $S_i$ is now generated from the 2D projection images $P_{\alpha j}$ (not noise filtered) generated by pre-processing from the 2D projection data sets $D_{\alpha j}$. This reconstruction is advantageously implemented with the use of filtered back-projection of the 2D projection images $P_{\alpha j}$, wherein a ramp filter is advantageously used as a filter. Moreover, in order to not suppress high frequencies, the individual pixels of the 2D projection images are processed without binning. The microcalcifications are now segmented in the slice images $S_i$ generated in this manner, meaning that those voxels that reflect microcalcifications are identified as microcalcium voxels. These are normally voxels whose greyscale values exceed a predetermined limit value.

Figure 3:
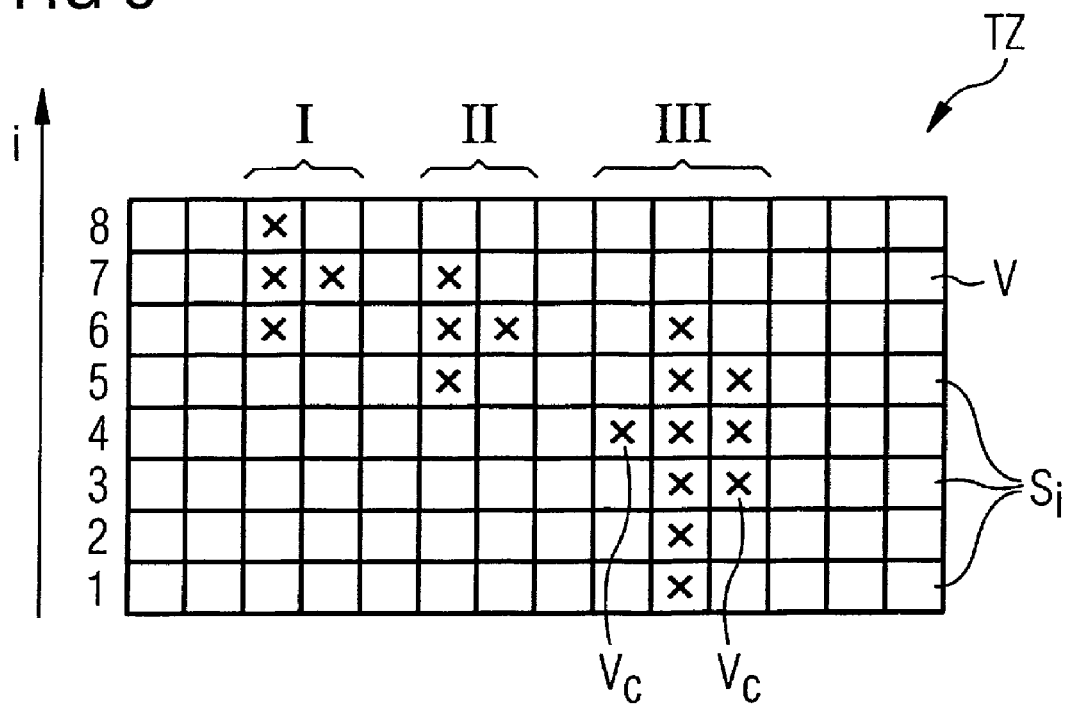
FIG. 3 shows a slice through a tomosynthetic 3D intermediate image, perpendicular to the projection plane, with microcalcifications marked therein in accordance with the invention.

This segmentation is illustrated using the example of FIG. 3. There three microcalcium regions I, II, III spatially separated from one another have been identified via segmentation in the 3D intermediate image TZ, wherein for clarity only the voxels V in plane perpendicular to the acquisition plane of the x-ray receiver are shown. The (segmented) voxels V identified as microcalcium voxels $V_c$ are marked by crosses. It can be seen from FIG. 3 that the microcalcium regions I, II, III extend across multiple slices i, i.e. occur in multiple slice images $S_i$ adjacent to one another.

In a next step, for each of these segmented microcalcifications or microcalcium regions I, II, III (FIG. 3) at least one subject slice image $S_{i=k}$ is now identified for this microcalcification according to FIG. 2. In each slice image $S_i$, the intensities or greyscale values of the microcalcium voxels $V_c$ associated with the respective microcalcium regions are determined in each slice image $S_i$ for the determination of this at least one subject slice image $S_{i=k}$. The subject slice image $S_{i=k}$ is then the slice image in which the voxel is located whose intensity or greyscale value is maximal (corresponding to a maximal absorption of the x-ray beam). In the example, the sought subject slice image is the slice image $S_4$ associated with the slice i=4.

Figure 4:
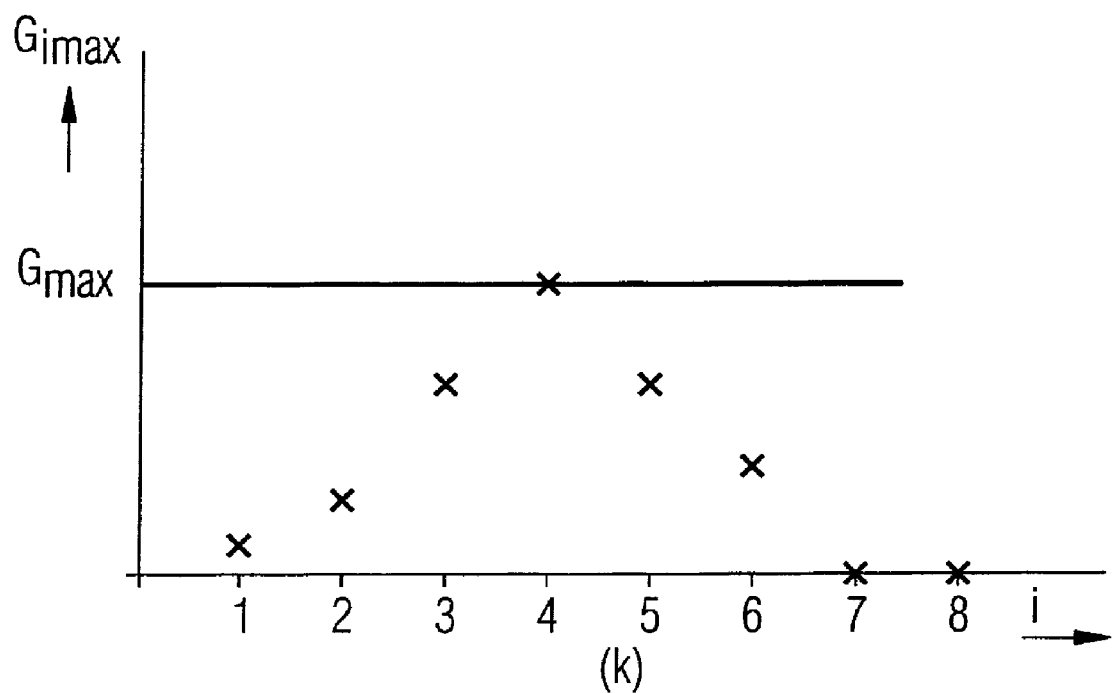
FIG. 4 is a diagram in which the greyscale value of the voxel whose greyscale value is maximal in this slice image is plotted for a microcalcification for each slice image.

The selection of the at least one subject slice image is exemplarily illustrated in FIG. 4 for the microcalcium region III. In FIG. 4 the greyscale value $G_{i,max}$ of that microcalcium voxel of the microcalcium region III whose greyscale value (intensity) is maximal in the slice image $S_i$ associated with this slice is plotted for each slice i. The at least one sought subject slice image $S_K$ is now the slice image $S_i$ whose microcalcium volume $V_c$ with the maximal greyscale value $G_{i,max}$ has the highest greyscale value $G_{max}$. In the example, the microcalcium voxel $V_c$ with the highest greyscale value $G_{max}$ is located in the slice i=4, such that the at least one sought subject slice image $S_k$ is the slice image $S_4$ associated with the slice i=4.

In the example, two slices i=5 and i=3 in which microcalcium voxels $V_c$ with high greyscale values G occur are adjacent to the slice i=4. In this case it can be appropriate to select at least the immediately adjacent slice images $S_3$ and $S_5$ as additional subject slice images instead of a single subject slice image $S_4$. The selection of multiple adjacent slice images is in particular also appropriate when it can be estimated from the areal expanse of the microcalcium voxels $V_c$ in a slice that the microcalcifications extend across multiple slices.

At least one subject slice image $S_K$ is determined in this way for each microcalcium region I, II, III. In the shown example, for example, this can be the slice images $S_2$ or, respectively, $S_3$ for the remaining microcalcium regions I, II.

Instead of the procedure to locate the at least one subject slice image that is explained using FIG. 4, it is also possible to select as a subject slice image that slice image in which the number of microcalcium voxels is greatest.

According to FIG. 2, only the microcalcium voxels $V_c$ belonging in these subject slice images $S_k$ (in the example $S_2$, $S_3$, $S_{3,4,5}$) are now projected forward in the 2D projection images $P_{\alpha j}$ (an operation inverse to the back-projection), and the pixels associated with these microcalcium voxels $V_c$ are marked as microcalcium pixels in the 2D projection images $P_{\alpha j}$. The microcalcium pixels belonging to the microcalcium regions I, II, III are localized and marked in all 2D projection images $P_{\alpha j}$ in this way. This forward projection and marking is implemented for every microcalcium region I, II, III segmented in the slice images $S_i$, and therefore also for every subject slice image $S_k$ or subject slice images $S_k$ respectively associated with these.

The intensities or greyscale values calculated in this forward projection are not used for correction of the 2D projection images $P_{\alpha j}$, but rather exclusively for their marking. The 2D projection images $P_{\alpha j}$ marked in this manner are subjected in a next step to an adaptive noise filtering. The microcalcium pixels (i.e. the 2D microcalcium regions associated with the (3D) microcalcium regions I, II, III of the tomosynthetic intermediate image TZ and marked in the 2D projection images $P_{\alpha j}$) are thereby either not noise-filtered or are subjected to a weaker noise filtering, i.e. a noise filtering in which the image noise is suppressed only to a lesser degree than in the image regions lying outside the 2D microcalcium regions associated with the microcalcium pixels.

With the use of a filtered back-projection in which high frequencies are emphasized, the final tomosynthetic 3D x-ray image is now generated from the 2D projection images $P_{\alpha j,fil}$ that have been noise-filtered in the described manner.

Although modifications and changes may be suggested by those skilled in the art, it is the intention of the inventors to embody within the patent warranted hereon all changes and modifications as reasonably and properly come within the scope of their contribution to the art.

We claim as our invention:

1. A tomosynthetic image reconstruction method comprising the steps of:
   reconstructing a tomosynthetic 3D intermediate image from a plurality of slice images respectively obtained from a plurality of digital 2D projection images respectively acquired from different projection angles relative to a subject in a limited angle range, without subjecting said slice images to noise filtering;
   segmenting microcalcium regions contained in the respective slice images and electronically marking microcalcium voxels respectively associated with said microcalcium regions;
   selecting at least one of said slice images as at least one subject slice image relevant to said microcalcium region;
   forward projecting the microcalcium voxels in the segmented microcalcium region of the at least one subject slice image, and marking microcalcium pixels associated with the microcalcium voxels in the 2D projection images;
   generating noise-filtered 2D projection images by subjecting the microcalcium pixels of the 2D projection images to adaptive noise filtering; and
   generating a final tomosynthetic 3D x-ray image from the noise-filtered 2D projection images.

2. A method as claimed in claim 1 comprising edge-filtering the marked microcalcium regions.

3. A method as claimed in claim 1 comprising reconstructing the tomosynthetic 3D intermediate image by filtered back-projection.

4. A method as claimed in claim 3 comprising emphasizing high frequencies in the filtered back-projection.

5. A method as claimed in claim 1 comprising reconstructing the final tomosynthetic 3D x-ray image by filtered back-projection.

6. A method as claimed in claim 5 comprising emphasizing high frequencies in the filtered back-projection.

7. A diagnostic mammography apparatus comprising:
   an x-ray tube and an x-ray detector configured to receive an examination subject therebetween, said x-ray tube being movable through a limited angle range relative to the subject;
   said x-ray tube and said x-ray detector being configured to generate a plurality of digital 2D projection images respectively at different projection angles relative to the subject within said limited angle range; and
   a processor supplied with said 2D projection images, said processor being configured to reconstruct a tomosynthetic 3D intermediate image from a plurality of slice images respectively obtained from said plurality of digital 2D projection images, without subjecting said slice images to noise filtering, segment microcalcium regions contained in the respective slice images and electronically marking microcalcium voxels respectively associated with said microcalcium regions, select at least one of said slice images as at least one subject slice image relevant to said microcalcium region, forward project the microcalcium voxels in the segmented microcalcium region of the at least one subject slice image, and mark microcalcium pixels associated with the microcalcium voxels in the 2D projection images, generate noise-filtered 2D projection images by subjecting the microcalcium pixels of the 2D projection images to adaptive noise filtering, and to generate a final tomosynthetic 3D x-ray image from the noise-filtered 2D projection images.

* * * * *